US00PP32184P2

(12) United States Plant Patent
Brazelton et al.

(10) Patent No.: US PP32,184 P2
(45) Date of Patent: Sep. 15, 2020

(54) ***VACCINIUM* PLANT NAMED 'ZF06-089'**

(50) Latin Name: *Vaccinium corymbosum*
Varietal Denomination: ZF06-089

(71) Applicant: The Conard-Pyle Company, West Grove, PA (US)

(72) Inventors: David M. Brazelton, Walterville, OR (US); Adam L. Wagner, Eugene, OR (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/602,378

(22) Filed: Sep. 26, 2019

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ..... A01H 5/08; A01H 6/36
See application file for complete search history.

(56) References Cited

U.S. PATENT DOCUMENTS

PP19,381 P2 10/2008 Lyrene
PP23,325 P2 1/2013 Brazelton et al.

*Primary Examiner* — Annette H Para
(74) *Attorney, Agent, or Firm* — Panitch Schwarze Belisario & Nadel LLP

(57) ABSTRACT

A new and distinct variety of *Vaccinium* plant, herein referred to by its cultivar name, 'ZF06-089', is provided which displays greenish-white colored inflorescence. The flower bud just before opening is oval shape and the leaves are ovate shape. The foliage is medium green colored. Moderately vigorous, spreading to compact growth habit is exhibited.

1 Drawing Sheet

Botanical/commercial classification:
Latin name of genus and species of plant claimed: *Vaccinium corymbosum.*
Variety denomination: 'ZF06-089'.

BACKGROUND OF THE INVENTION

The present invention relates to a new and distinct cultivar of *Vaccinium* plant botanically known as *Vaccinium corymbosum* and hereinafter referred to by the cultivar name 'ZF06-089'.

The new cultivar originated in a controlled breeding program in Lowell, Oreg. during April 2003. The objective of the breeding program was the development of superior *Vaccinium* cultivars that meet the evolving needs of the blueberry and home enthusiast industries.

The new *Vaccinium* cultivar is the result of cross-pollination. The female parent (i.e., seed parent) of the new cultivar is 'Toro', (non-patented) and is characterized by its pink to white colored inflorescences, dark green foliage color, and moderate growth vigor with a stocky and compact growth habit. The male parent (i.e., pollen parent) of the new cultivar is 'FLX-2' (U.S. Plant Pat. No. 19,381) and is characterized by its pink to white colored inflorescences, blue-green colored foliage, and moderate growth vigor with spreading growth habit.

The parentage can be summarized as follows:

'Toro' x 'FLX-2'

The new cultivar was obtained and selected as a single flowering plant within the progeny of the above stated cross-pollination during July 2008 in a controlled environment in Lowell, Oreg.

Asexual reproduction of the new cultivar by softwood stem cuttings since 2012 in Lowell, Oreg. has demonstrated that the new cultivar reproduces true to type with all of the characteristics, as herein described, firmly fixed and retained through successive generations of such asexual propagation.

SUMMARY OF THE INVENTION

The new cultivar of the present invention possesses the following combination of characteristics, which have been repeatedly observed and can be used to distinguish 'ZF06-089' as a new and distinct cultivar of *Vaccinium* plant:

(a) provides greenish-white colored inflorescences,
(b) exhibits medium green colored foliage, and
(c) forms moderately vigorous, spreading to compact growth habit.

The new variety can be readily distinguished from its ancestors. More specifically, 'Toro' (i.e., seed parent) exhibits a less prostrate growth habit and produces a higher yield of fruit compared to the new variety and forms pink to white colored inflorescence whereas the new variety forms greenish-white colored inflorescence. Additionally, 'FLX-2' (i.e., pollen parent) exhibits a decreased hardiness and narrower leaves compared to the new variety and forms blue-green colored foliage, whereas the new variety forms medium green colored foliage. Moreover, the new variety can be readily distinguished from non-parental related similar varieties. Of the many commercially available *Vaccinium* cultivars, the most similar in comparison to the new cultivar is 'ZF06-043' (U.S. Plant Pat. No. 23,325). However, plants of the new cultivar differ from plants of 'ZF06-043' in at least the following characteristics:

1. Plants of the new cultivar have a more uniform and spreading growth habit than plants of 'ZF06-043';
2. Plants of the new cultivar have larger foliage than plants of 'ZF06-043'.

BRIEF DESCRIPTION OF THE PHOTOGRAPH

The accompanying photograph shows, as nearly true as it is reasonably possible to make the same in color illustrations of this type, a typical specimen of the new variety. The illustrated *Vaccinium* plant of the new variety was approximately three years of age and was grown in the ground in Lowell, Oreg. during July 2017.

FIG. 1—illustrates a top view of a plant of 'ZF06-089' growing in the ground.

DETAILED BOTANICAL DESCRIPTION

The chart used in the identification of colors described herein is that of The Royal Horticultural Society (R.H.S. Colour Chart, London, England, 2015 edition), except where general color terms of ordinary significance are used. The terminology which precedes reference to the chart has been added to indicate the corresponding color in more common terms. The color values of the flowers were determined in April 2019 and the color values of all other plants parts were determined in July 2019 under natural light conditions in Cochranville, Pa. Measurements and numerical values represent averages of typical plants.

Plant:

*Growth habit and general appearance*.—Moderately vigorous, spreading and compact growth habit.

*Size*.—Height from soil level to top of plant plane is approximately 40.0 cm. — Width: approximately 60.0 cm.

*Branching habit*.—Freely branching. Pinching enhances branching. — Quantity of lateral branches per plant approximately 5 main branches.

*Branch*.—Strength: strong. — Length: approximately 40.0 cm. — Diameter: approximately 1.0 cm. — Length of central internode: approximately 2.0 cm. — Texture: mostly smooth with some rough areas where the wood is starting to become harder. — Color of mature stems: commonly mostly near Yellow-Green Group 146B with some fissures of near Grey-Brown Group N199B and near Grey Group 201C where the wood is starting to become harder.

Foliage:

*General description*.—Fragrance: none detected. — Form: simple. — Arrangement: alternate.

*Leaves*.—Shape: ovate. — Margin: entire. — Apex: acute. — Base: cuneate. — Venation pattern: pinnate. — Length of mature leaf: approximately 5.5 cm. — Width of mature leaf: approximately 3.5 cm. — Texture of upper and lower surfaces: glabrous. — Color of upper surface of young foliage: commonly near Yellow-Green Group 144A with overtones of near Greyed-Orange Group 171A near the apex and margin with indistinguishable venation. — Color of lower surface of young foliage: commonly near Yellow-Green Group 144B with overtones of near Greyed-Orange Group 171B near the apex with indistinguishable venation. — Color of upper surface of mature foliage: commonly near Green Group 137B with venation of near Green Group 137C. — Color of lower surface of mature foliage: commonly near Green Group 138B with venation of near Green Group 138A.

*Petiole*.—Length: approximately 3.0 mm. — Diameter: approximately 2.0 mm. — Texture: glabrous. — Color: commonly near Yellow-Green Group 144A.

Flowering:

*Flowering season*.—Flowers in spring in southeastern Pennsylvania.

*Lastingness of individual inflorescence on the plant*.—Approximately one week.

Flower:

*General description*.—Shape: urceolate. — Quantity per plant approximately 250 fully open on a plant at a given time. — Fragrance: none noticeable. — Aspect: pendulous.

*Bud just before opening*.—Shape: oval. — Length: approximately 1.0 cm. — Diameter: approximately 0.5 cm. — Color: commonly close to Green-White Group 157A.

*Corolla*.—Color: commonly near Green-White Group 157A. — Length: approximately 8.0 mm. — Width: approximately 6.0 mm. — Aperture width: approximately 5.0 mm.

*Calyx*.—Shape: star-shaped. — Depth: approximately 3.0 mm. — Diameter: approximately 6.0 mm.

*Sepals*.—Quantity 5. — Shape: ovate. — Margin: entire. — Apex: acute. — Base: fused. — Length: approximately 4.0 mm. — Width: approximately 2.0 mm. — Texture of upper surface: glabrous. — Texture of lower surface: glabrous. — Color of upper and lower surfaces: commonly near Green-White Group 157A.

*Reproductive organs*.—

*Androecium*.—Stamen quantity per flower approximately 11. — Stamen length: approximately 5.0 mm. — Anther shape: narrow oblong. — Anther length: approximately 3.0 mm. — Anther color: commonly near Greyed-Orange Group 165B. — Pollen amount: not observed.

*Gynoecium*.—Pistil quantity 1 per flower. — Pistil length: approximately 7.0 mm. — Stigma shape: flat disk. — Stigma color: commonly near Yellow-Green Group 145A. — Style length: approximately 5.5 mm. — Style color: commonly near Yellow-Green Group 145A. — Ovary length: approximately 1.0 mm. — Ovary color: commonly near Yellow-Green Group 146B.

Development:

*Disease and pest resistance*.—Resistance to pathogens and pests common to *Vaccinium* has not been observed.

*Commercial crop time*.—Approximately one year from a rooted cutting to finish in a one-gallon container.

*Hardiness*.—USDA Zone 5.

The new cultivar has not been observed under all possible environmental conditions to date. Accordingly, it is possible that the phenotype may vary somewhat with variations in the environment, such as temperature, light intensity, and day length, without, however, any variance in genotype.

We claim:

1. A new and distinct cultivar of *Vaccinium* plant characterized by the following combination of characteristics:

(a) provides greenish-white colored inflorescences, (b) exhibits medium green colored foliage, and (c) forms moderately vigorous, spreading to compact growth habit;

substantially as herein shown and described.

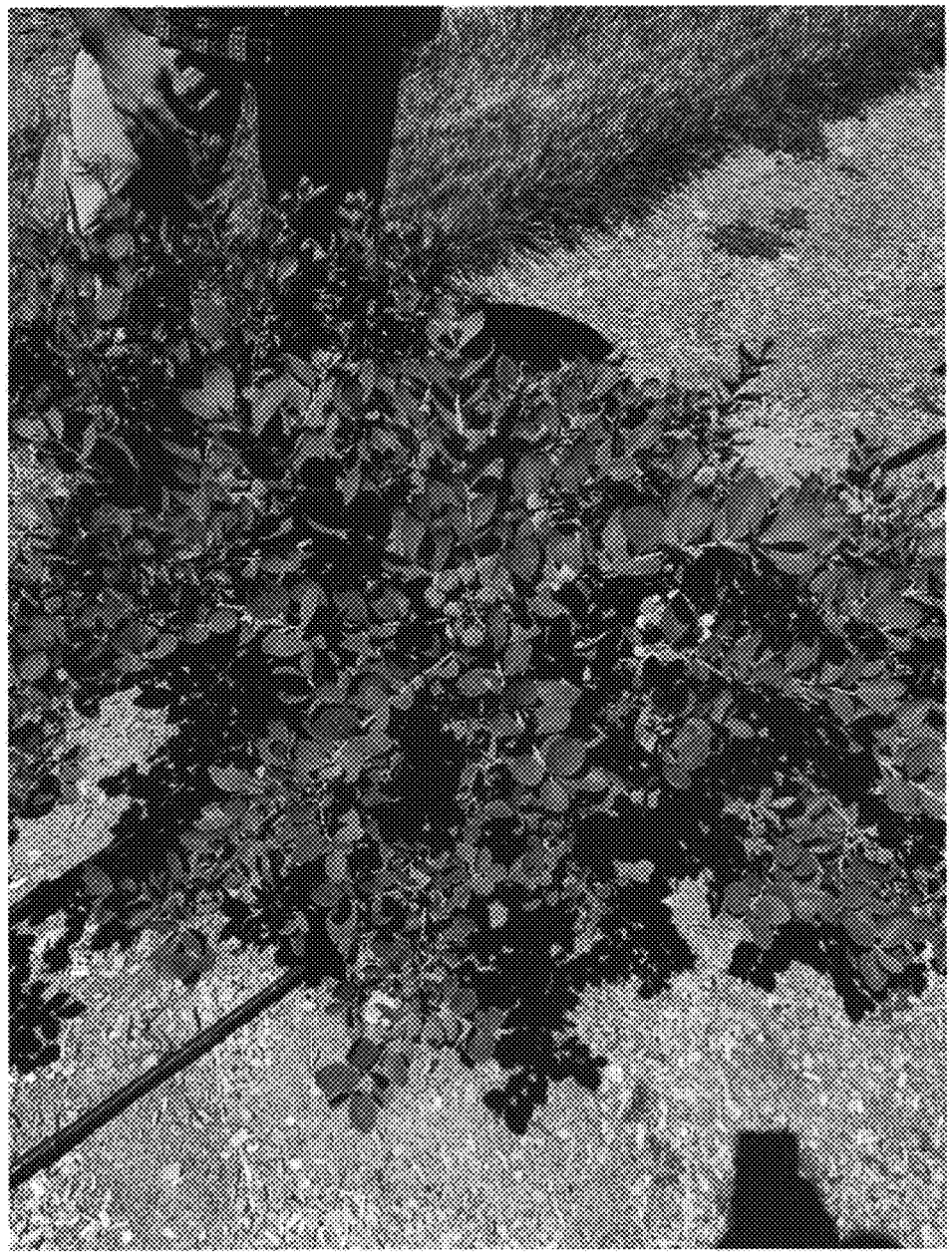

* * * * *